United States Patent [19]

Winter et al.

[11] 4,303,689
[45] Dec. 1, 1981

[54] FLAVORING WITH PYRAZINE DERIVATIVES

[75] Inventors: Max Winter, Petit-Lancy; Fritz Gautschi, Commugny; Ivon Flament; Max Stoll, both of Petit-Lancy, all of Switzerland; Irving M. Goldman, Niantic, Conn.

[73] Assignees: Firmenich SA, Geneva, Switzerland; General Foods Corporation, White Plains, N.Y.

[21] Appl. No.: 243,850

[22] Filed: Apr. 13, 1972

Related U.S. Application Data

[60] Division of Ser. No. 70,560, Sep. 8, 1970, Pat. No. 3,702,253, which is a continuation of Ser. No. 543,069, Apr. 18, 1966, abandoned, which is a continuation-in-part of Ser. No. 452,342, Apr. 30, 1965, abandoned.

[51] Int. Cl.$^3$ ............................................. A23L 1/234
[52] U.S. Cl. .................................................... 426/537
[58] Field of Search ......................................... 426/537

[56] References Cited

U.S. PATENT DOCUMENTS 1,696,419 12/1928 Staudinger et al. .................. 426/534
3,579,353 5/1971 Nakel et al. .......................... 426/537

OTHER PUBLICATIONS

Kleinfield, The Washington Star, Sunday, Dec. 4, 1977, pp. G–1, G–6.
Fenaroli's Handbook of Flavor Ingredients, 2nd Ed., 1975, vol II Edited by Furia et al., CRC Press; Cleveland, pp. 663, 870, 871.
Bedoukian, Progress in Perfumery Materials, Cosmetics and Perfumery, Apr. 1973, p. 31.
Decision of the Federal Patent Court (Patent Office of the Federal Republic of Germany, 32nd Senate of 10/31/72, Reference 32W (pag) 32/71.

*Primary Examiner*—Joseph M. Golian

[57] ABSTRACT

The subject matter relates to flavoring with a composition of matter consisting essentially of a pyrazine derivative having the following formula:

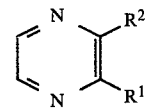

wherein
(a) $R^1$ is a methyl group and $R^2$ is either an alkyl group having from 2 to 6 carbon atoms which can be branched at the chain end when said chain has 3 or 4 carbon atoms, or a vinyl, a thienyl-2 or a pyrryl-1 group; or
(b) $R^1$ is an ethyl group and $R^2$ is an ethyl or a vinyl group.

3 Claims, No Drawings

FLAVORING WITH PYRAZINE DERIVATIVES

This application is a division of application Ser. No. 70,560, filed Sept. 8, 1970, now U.S. Pat. No. 3,702,253, which application was a continuation of application Ser. No. 543,069, filed Apr. 18, 1966 and now abandoned, which latter application was a continuation-in-part of application Ser. No. 452,342, filed Apr. 30, 1965 and also now abandoned.

The invention relates to flavor agents in general. More particularly the invention relates to chemical compounds or compositions which have been found to have utility in the alteration of flavor or flavor characteristics of substances, whether naturally occurring or synthetic. Still more particularly the invention relates to a group of chemical compounds which have been found to be useful in the area of flavor-note alteration, whether by the enhancement of flavors or flavor-notes that are characteristic in a substance, by the alteration of a flavor or a flavor-note from a less to a more desirable one, or by the complete or partial masking of a flavor or flavor-note.

As is generally recognized by those familiar with the art, the science of flavor technology is an extremely complex one. Although much is known about flavor and flavor technology there is still a great deal to be learned in the field and the body of scientific literature is being rapidly expanded by those working in the area. The technology of flavor synthesis and blending of various flavor elements to achieve certain desirable results is of great commercial importance at the present stage of industrial advance. Commercial production of consumer goods from synthetic starting materials is becoming more and more common, and desirable, as world population continues to increase its demands upon the finite capacity for the production of natural products. Industry is also continually seeking means of upgrading natural products—methods of altering or enhancing the qualities of taste of less desirable natural products—usually more abundant—into more desirable product qualities. Often, for example, a product can be made commercially attractive only by masking or blanking out an undesirable flavor component. Formerly, before the advent of the flavor chemist and his technology, this unit of production would have been lost, or at least, would have had to have been re-processed to a useable quality. By the use of specifically designed flavoring agents, however, the undesirable flavor note can be eliminated or masked with another desirable one, and the expensive and time-consuming re-processing step eliminated or the production batch saved for use. Too, it is common in some segments of the industry, particularly the food industry, to add flavor agents to production units to enhance or bring out a desirable flavor characteristics of products—and by so doing to render the product more desirable from a consumer preference standpoint.

It is the object of this invention therefore, to provide the flavor technologist with additional tools for his use in the alteration of food flavors, whether it be flavor or flavor-note alteration generally or the enhancement or improvement of flavor or flavor notes specifically.

It is a further object of the invention to furnish a group of chemical compositions which have utility in the technology of flavor alteration, whether added to solid or liquid compositions for human consumption, and which may be used in either solid or liquid form.

A further object of the invention is to describe a group of chemical compounds having desirable utility as flavor agents which may be prepared synthetically, thus enabling the food technologist to alter or enhance his product without drawing upon a natural product for the flavor agent.

A still further object of the invention is to describe a group of chemical compounds capable of synthesis from readily available organic substances which may be used singly or in combination to alter the flavor or flavor notes of compositions for food use, whether used in micro-quantities such as parts-per-million or in larger quantities, as the dictates of the end results may require.

Other objects will become apparent to those skilled in the art as the description proceeds.

Thus, in accordance with the concept of the instant invention, there is set out below a group of compounds which have been found to have utility as flavor agents and to represent valuable materials to the food technologist who wishes to alter the flavor components of foods or food products either liquid foods or beverages, such as fruit and vegetable juices, milk, coffee, tea, cocoa, chocolate, and the like or solid foods such as cereals, flours, confections, vegetables, meats, etc. The flavor agents may be used either in liquid or solid form and are used in quantities designed to give the desired results, as will be more clearly explained as the description proceeds.

The chemical compounds which have been found to have utility as flavor agents may be generally classified as pyrazine hydrocarbons.

The flavor agents or flavor modifying compositions of this invention are available to the food technologists in a variety of forms. It is usually preferable to use the agents in the form of a solution, for ease of dilution, exactitude of measurement, efficiency of distribution in the end use, etc. However the chemical nature of the compound, its solubility in acceptable solvents, its stability, and other characteristics may dictate the form in which it is used.

The amounts of the agents used is also subject to wide variation, of course. More concentrated materials, and those with the greatest degree of flavor modifying ability will be used in lesser amounts. Some degree of experimentation is, of course, required to achieve the desired results. A small, but flavor modifying amount, of the agents is blended with the material whose total flavor is to be altered, the amount depending upon the end result desired.

Two different types of methods were used in testing the compounds listed in this specification for their utility as flavor agents, flavor modifiers, flavor alteration agents, flavor-note enhancers, and the like. The first type method (A) served the purpose of determining the intrinsic taste, flavor and aroma of each individual compound. The second type methods (B) and (C) were used for testing the flavor- and aroma-modifying or -enhancing effects of the compounds hereinafter listed on coffee products and more particularly on spray-dried soluble coffee products commercially known as "instant coffee".

Method A

The vehicle used for testing the flavor compounds was a 65% solution of cane sugar in tap water. The flavor compounds were incorporated in this sugar syrup in the form of 1% or 1 per 1000 by weight solutions in 96% ethyl alcohol. The concentration of the flavor compounds in the sugar syrup varied between about 0.005 and 5 g. for 100 liters of syrup according to the varying strength of flavor compounds. Samples of each flavored sugar syrup were submitted to the members of the tasting panels. After tasting the samples each member had to give an evaluation of each flavor compound in terms of descriptive words.

In the evaluation of materials for the alteration or enhancement of coffee flavor or of coffee flavor notes it is essential that the equipment used, coffee pots, cups, spoons, measuring equipment, etc. be absolutely clean prior to use.

Method B

The coffee base was prepared by dissolving 1 g. of a commercial spray-dried soluble coffee in boiling water. A sufficient number of pots was prepared to provide one pot for each flavor agent to be evaluated plus one control. The flavor agent was added to the coffee base in the form of a 1% or 1 per 1000 by weight alcoholic solution at concentrations varying between 0.005 and 5 g. of flavor agent for 100 liters of coffee base. The measured quantity of the flavor agent was added to a pot of the coffee base material, stirred well, and poured immediately into cups for the organoleptic evaluation. The taste tests were made within a short time (not more than 15 minutes) after the final composition to be tested was prepared.

The organoleptic evaluation involved grading a series of cups that were coded, the taster merely rating the coded cups against the standard or control which did not contain the flavor agent. The standard was placed at the first position in a series of cups. The tasters were asked to ascertain whether or not there existed differences in the flavor of the samples to be tested as compared with the control. The tasters were furthermore asked to describe and characterize the various flavor notes and types determined.

Method C

Using boiling Crystal Spring Water, to provide a clean starting taste, a 1.35% solution of relatively bland tasting commercially available spray-dried soluble coffee was prepared. The containers used—preferably the lower portion of a glass coffee maker—was absolutely clean, as was the other equipment used, e.g. cups and spoons.

A sufficient number of containers, or pots, were used to accomodate each flavor fraction to be studied, plus one control. The flavor fraction was measured carefully with a micro-syringe, adding from 2 to 150 microliters of the flavor fraction per pot. The mixture of coffee solution and flavor fraction was stirred and immediately poured into cups for tasting. At least 5 experienced tasters are used. The tasting should begin at least within 15 minutes after the solution is prepared. If not, the solution should be discarded and fresh solution prepared.

The cups are coded and the samples are not identified. A standard sample is included in which no flavor fraction has been added. The taster is asked to identify and describe the flavor enhancement or modification noted.

In the following specific description of the pyrazine hydrocarbon compounds there is first given the structural formula followed by a list of members of the group which have been found to have outstanding utility in the concept of this invention. Immediately following the chemical name of each member there is given the commercial source or a literature reference giving a method for its preparation. Commercially available products will be identified by the abbreviation c.a., and may be obtained from FLUKA, A. G., Buchs S. G., Switzerland; ALDRICH CHEM. CO., Milwaukee, Wis.; DR. F. RASCHIG GMBH, Ludwigshafen a. Rh., West-Germany; or K & K LABORATORIES INC., Plainview, NY. 11803.

In those instances wherein new compounds are described a detailed method of preparation is given following the list of the group members. New compounds will be identified by the abbreviation n.c.

The results of the organoleptic evaluation tests are set out in the Tables following the detailed description of the compounds.

The pyrazine hydrocarbons are an important group of compounds which have been found to have exceptional utility as flavor agents in accordance with the instant inventive concept. Compounds of the group have the general formulae:

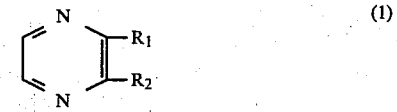
(1)

wherein $R_1$ is hydrogen, alkyl, 1-pyrrolyl or 2-thienyl; and $R_2$ is alkyl or alkenyl,

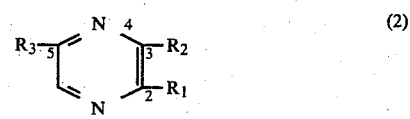
(2)

wherein $R_1$, $R_2$ and $R_3$ are alkyl groups having from 1 to 5 carbon atoms,

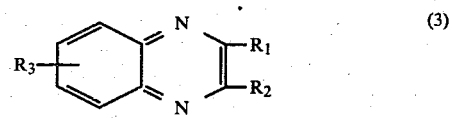
(3)

wherein $R_1$, $R_2$ and $R_3$ are hydrogen or methyl groups,

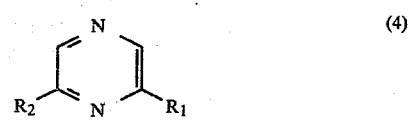
(4)

wherein $R_1$ and $R_2$ are alkyl groups containing from 1 to 3 carbon atoms,

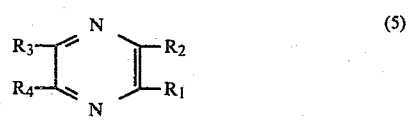
(5)

wherein $R_1$, $R_2$, $R_3$ and $R_4$ are alkyl groups containing from 1 to 6 carbon atoms, and

(6)

wherein $R_1$ is methyl or ethyl and $R_2$ is alkyl or alkenyl with $C_1$ to $C_6$.

Compounds of this group which are of special interest include:

(1)

a. 2-methyl-3-ethyl-pyrazine: n.c.
b. 2-methyl-3-isobutyl-pyrazine: n.c.
c. 2-methyl-3-propyl-pyrazine: n.c.
d. 2-methyl-3-isopropyl-pyrazine: n.c.
e. 2-methyl-3-butyl-pyrazine: n.c.
f. 2-methyl-3-amyl-pyrazine: n.c.

(1)

g. 2-methyl-3-hexyl-pyrazine: n.c.
h. 2,3-dimethyl-pyrazine: Ber. 40, 4855 (1907)
i. 2,3-diethyl-pyrazine: n.c.
j. 2-ethyl-3-vinyl-pyrazine: n.c.
k. 2-methyl-3(5,6)-(pyrrolyl-1)-pyrazine: n.c.
l. 2-methyl-3-(thienyl-2)-pyrazine: n.c.
m. 2-ethyl-pyrazine: J.Org.Chem.26, 3379 (1961)
n. 2-propyl-pyrazine: J.Org.Chem.26, 3379 (1961)
o. 2-isopropyl-pyrazine: J.Org.Chem.26, 3379 (1961)
p. 2-vinyl-pyrazine: J.Org.Chem.26, 3379 (1961)
q. 2-isopropenyl-pyrazine: n.c.
r. 2-methyl-3-vinyl-pyrazine: n.c.

(2)

a. trimethyl-pyrazine: J.A.C.S. 72, 844(1950)
b. 2,6-dimethyl-3-ethyl-pyrazine: n.c.
c. 2,5-dimethyl-3-ethyl-pyrazine: n.c.
d. 2,5-dimethyl-3-propyl-pyrazine: n.c.
e. 2,6-dimethyl-3-methyl-pyrazine: n.c.
f. 2,5-diethyl-3-methyl-pyrazine: n.c.
g. 2,5-dimethyl-3-butyl-pyrazine: n.c.
h. 2,3-dimethyl-5-isoamyl-pyrazine: n.c.
i. 2,5-dimethyl-3-isoamyl-pyrazine: n.c.
j. 2,3-diethyl-5-methyl-pyrazine: n.c.

(3)

a. 5-methyl-quinoxaline: Ann.237, 336 (1887)
b. 2-methyl-quinoxaline: Org.Synth.30,86 (1950)
c. 6-methyl-quinoxaline: Ann. 237, 336 (1887)
d. 2,3-dimethyl-quinoxaline: Ber. 40, 4852 (1907)
e. 2-methyl-3-ethyl-quinoxaline: Ber. 22, 526 (1889)
f. 2,3-diethyl-quinoxaline: J.A.C.S.79,1712 (1957)

(3)

g. 2-methyl-3-propyl-quinoxaline: J.Chem.Soc. 1946, 54
h. 2-methyl-3-isopropyl-quinoxaline: J.Chem.Soc. 1953, 2822
i. 2-methyl-3-butyl-quinoxaline: n.c.
j. 2-methyl-3-isobutyl-quinoxaline: n.c.
k. 2-methyl-3-amyl-quinoxaline: J.Chem.Soc. 1943, 322
l. 2-ethyl-quinoxaline: J.Chem.Soc.1953, 2822

(4)

a. 2-methyl-6-ethyl-pyrazine: n.c.
b. 2-methyl-6-propyl-pyrazine: J.Org.Chem. 27, 1355 (1962)
c. 2,6-diethyl-pyrazine: n.c.
d. 2-methyl-6-vinyl-pyrazine: n.c.

(5)

a. trimethyl-butyl-pyrazine: n.c.
b. trimethyl-isoamyl-pyrazine: n.c.
c. 2,5-dimethyl-3,6-dipropyl-pyrazine: n.c.
d. 2,5-dimethyl-3,6-diisopropyl-pyrazine: n.c.
e. 2,5-dimethyl-3,6-dibutyl-pyrazine: n.c.
f. 2,5-dimethyl-3,6-diisobutyl-pyrazine: n.c.
g. 2,5-dimethyl-3,6-diamyl-pyrazine: n.c.
h. 2,5-dimethyl-3,6-dihexyl-pyrazine: n.c.
i. 2,3,5-trimethyl-6-hexyl-pyrazine: n.c.
j. 2,5-dimethyl-3,6-diethyl-pyrazine: n.c.

(6)

a. 2-ethyl-5-methyl-pyrazine: n.c.
b. 2-isopropyl-5-methyl-pyrazine: n.c.
c. 2,5-diethyl-pyrazine: n.c.
d. 2-methyl-5-vinyl-pyrazine: n.c.

Organoleptic evaluations are set out in Table I below
The new compounds can be prepared as follows:

The 2,3-disubstituted pyrazines (formula (1)) can be obtained by a method comprising catalytically dehydrogenating with copper chromite the correspondingly substituted dihydropyrazines which, in turn, can be prepared by condensation of ethylene diamine with the corresponding alpha-diketones. By way of illustration the preparation of 2-methyl-3-ethyl-pyrazine is described in more details.

(1)

a. 2-Methyl-3-ethyl-pyrazine. In a 3-necked flask equipped with a stirrer, means for cooling and a dropping funnel there was placed 150 g. of ethylene diamine in 500 ml. ether. After cooling to 0° C. there was slowly added with stirring a solution of 250 g. of ethyl methyl diketone in 500 ml. of ether. After the addition was complete, the temperature was allowed to rise to room temperature and the mixture was heated on a water bath for a few minutes. The material separated into 2 phases and the water phase was discarded. The ether phase was dried with sodium sulfate, the solvent was removed by evaporation and the residue distilled under reduced pressure and an inert atmosphere. There was obtained 192 g. of the dihydropyrazine (62% yield), boiling point 61°–65° C./11 mm. Hg.

In an apparatus similar to that described by Bouveault in Bull IV, 3, 119 (1908) the dihydro pyrazine was distilled under reduced pressure under nitrogen atmosphere through a column containing copper chromite (Girdler G-13). The catalyst was heated to 300° C. electrically and the effluent was passed through a Widmer column to separate the unhydrogenated material.

The product was condensed, dried and redistilled; a 90% yield was obtained of a product boiling at 57° C./10 mm.Hg.

The same method as used for compound (1) a. was applied for the preparation of the following compounds:

(1)

b. 2-methyl-3-isobutyl-pyrazine: b.p. 74°/10 mm. Hg.

(1)

c. 2-methyl-3-propyl-pyrazine: b.p. 71°–72°/10 mm. Hg.

(1)

d. 2-methyl-3-isopropyl-pyrazine: b.p. 59°/10 mm. Hg.

(1)

e. 2-methyl-3-butyl-pyrazine: b.p. 83°–84°/9 mm. Hg.

(1)

f. 2-methyl-3-amyl-pyrazine: b.p. 98°/10 mm. Hg.

(1)

g. 2-methyl-3-hexyl-pyrazine: b.p. 113°–115°/9 mm.Hg.

(1)

i. 2,3-diethyl-pyrazine: b.p. 69°–71°/12 mm. Hg.

(1)

j. 2-Ethyl-3-vinyl-pyrazine can be prepared from 2-ethyl-3-methyl-pyrazine by the method described in J.Org.Chem. 27, 1363 (1962). B.P. 75°–80° C./10 mm.Hg.

(1)

k. 2-Methyl-3(5,6)-(pyrrolyl-1)-pyrazine can be prepared as follows: N-Pyrrolyl-lithium is prepared by reacting 0.242 mole (15.4 g.) of butyllithium (as 15% suspension in hexane) with 0.22 mole (14.7 g.) of pyrrole at −20° C. in the presence of 100 ml. of tetrahydrofuran. There is then added at room temperature a solution of 0.2 mole (25.6 g.) of 3(5,6)-chloro-2-methyl-pyrazine [obtained by the method described in J.Org.Chem. 26, 2356 (1961)] in 75 ml. of tetrahydrofuran. The reaction mixture is refluxed for 5 days and subjected to the usual treatments for purifying and isolating the reaction product which is then distilled. There is thus obtained 2-methyl-3(5,6)-N-pyrrolyl-pyrazine as a fraction distilling at 120°–124° C./10 Torr.

(1)

l. 2-(Thienyl-2)-3-methyl-pyrazine is prepared as follows. A solution of 0.36 g. (0.006 mole) of ethylene diamine in 3 ml. of ether is cooled to 0° C. To this solution there is added slowly in a nitrogen atmosphere a solution of 0.94 g. (0.006 mole) of (thienyl-2) methyl diketone (obtained by oxidation of 2-propionylthiophene with selenium dioxide) in 3 ml. of absolute ether. The ether is gradually replaced by benzene, and water is removed as an azeotropic mixture with the latter solvent. The reaction product is fractionally distilled, and the fraction boiling at 85°–105° C./0.003 mm. Hg. is redistilled through a copper chromite column (GIRDLER G-13) heated at 350° C. There is thus obtained 2-(thienyl-2)-3-methyl-pyrazine of b.p. 94° C./0.03 mm. Hg.

(1)

q. 2-Isopropenyl-pyrazine is obtained from 2-ethyl-pyrazine by the method described in J.Org.Chem. 27, 1363 (1962). It has the following peaks in the MS: 119 (100%), 120 (81%) and 67 (21%).

(1)

r. 2-Methyl-3-vinyl-pyrazine is prepared from 2,3-diethylpyrazine by the same method as used for compound (1) q. It has a b.p. 66°–67° C./13 mm. Hg.

(2)

b. 2,6-Dimethyl-3-ethyl-pyrazine is prepared by the addition of an ethyl group at the 3-position of 2,6-dimethylpyrazine by the alkyl-lithium method described by Klein et al. in J.A.C.S. 73, 2949 (1951). The resulting product has a b.p. of 64°–66° C./8 mm. Hg.

(2)

c. 2,5-Dimethyl-3-ethyl-pyrazine is prepared by the addition of an ethyl group at the 3-position of 2,5-dimethyl-pyrazine by the alkyl-lithium method described by Klein et al. (loc. cit.). The resulting product has a b.p. of 63°–68° C./8 mm. Hg.

(2)

d. 2,5-Dimethyl-3-propyl-pyrazine is prepared by the addition of an n-propyl group at the 3-position of 2,5-dimethylpyrazine by the alkyl-lithium method described by Klein et al. (loc.cit.). The product is identified by mass spectrometry. It has a b.p. of 80° C./10 mm. Hg.

(2)

e. 2,6-Diethyl-3-methyl-pyrazine is prepared by the introduction of a methyl group into the 3-position of 2,6-diethylpyrazine by the method of Klein et al. (loc.cit.). The product has a b.p. of 91°–92° C./13 mm. Hg.

(2)

f. 2,5-Diethyl-3-methyl-pyrazine is prepared by the introduction of a methyl group into the 3-position of 2,5-diethylpyrazine by the method of Klein et al. (loc.cit.). The product was isolated by gas chromatography and was identified by mass spectrometry.

(2)

g. 2,5-Dimethyl-3-butyl-pyrazine is prepared by introducing a butyl group into the 3-position of 2,5-dimethylpyrazine by the method of Klein et al. (loc.cit.). The resulting product has a b.p. of 91° C./9 mm. Hg.

(2)

h. 2,3-Dimethyl-5-isoamyl-pyrazine is prepared by introducing an isoamyl group into the 5-position of 2,3-dimethylpyrazine by the method of Klein et al. (loc.cit.). The product is identified by mass spectrometry.

(2)

i. 2,5-Dimethyl-3-isoamyl-pyrazine is prepared by introducing an isoamyl group into the 3-position of 2,5-dimethylpyrazine by the method of Klein et al. (loc.cit.). The product has a b.p. of 110°–120° C./13 mm. Hg.

(2)

j. 2,3-Diethyl-5-methyl-pyrazine is prepared by the method described for the preparation of compound (1) a., using 1,2-diamino-propane instead of ethylene diamine and dipropionyl as the α-diketone. The product has a b.p. of 79°–80° C./12 mm.Hg.

(3)

i. 2-Methyl-3-butyl-quinoxaline is obtained by the same method as compound (3) d. It has a b.p. of 153° C./9 mm. Hg.

(3)

j. 2-Methyl-3-isobutyl-quinoxaline is obtained by the same method as compound (3) e. It has a m.p. 94°–95° C.

(4)

a. 2-Methyl-6-ethyl-pyrazine was obtained by the alkylation of 2,6-dimethyl-pyrazine by the method described by Levine and Behun in J.Org.Chem. 26, 3379 (1961). It has a boiling point of 54°–57° C./11 mm. Hg.

(4)

c. 2,6-Diethyl-pyrazine was obtained by subjecting compound (4) a. to a second alkylation by the procedure described above. It has a boiling point of 70° at 10 mm. Hg.

(4)

d. 2-Methyl-6-vinyl-pyrazine is obtained by starting with 2,6-dimethyl-pyrazine and following the method of Levine et al. reported in J.Org.Chem. 27, 1363 (1962). It has a b.p. of 74°–75°/22 mm. Hg.

(5)

a. 2,3,5-Trimethyl-6-butyl-pyrazine was prepared by introducing a butyl group into the 6-position of 2,3,5-trimethylpyrazine by the method of Klein et al. (loc.cit.). The product was isolated by gas chromatography and identified by mass spectrometry.

(5)

b. 2,3,5-Trimethyl-6-isoamyl-pyrazine was prepared by introducing an isoamyl group into the 6-position of 2,3,5-trimethyl-pyrazine by the method of Klein et al. (loc.cit.). The product had a b.p. of 80° C./10 mm.Hg.

(5)

c. 2,5-Dimethyl-3,6-dipropyl-pyrazine was prepared by first forming 3-oximino-2-hexanone by reacting 2-hexanone with nitrosyl chloride according to the method of BOUVEAULT, Bull. [3] 31, 1163 (1904). The autocondensation of two molecules of the imino-ketone in the presence of zinc and acetic acid [according to the method described in Chimia 11, 310 (1957)] yielded 2,5-dimethyl-3,6-dipropyl-pyrazine which had a b.p. of 109°–110° C./10 mm. Hg.

(5)

d. 2,5-Dimethyl-3,6-diisopropyl-pyrazine was prepared by first forming 4-methyl-3-oximino-2-pentanone by reacting 4-methyl-2-pentanone with nitrosyl chloride according to the method of BOUVEAULT, Bull. [3] 31, 1163 (1904). The autocondensation of two moles of the imino-ketone in the presence of zinc and acetic acid [according to the method described in Chimia 11, 310 (1957)] yielded 2,5-Dimethyl-3,6-diisopropyl-pyrazine which had a b.p. of 91° C./8 mm. Hg.

(5)

e. 2,5-Dimethyl-3,6-dibutyl-pyrazine was prepared by first forming 3-oximino-2-heptanone by reacting 2-heptanone with nitrosyl chloride according to the method of BOUVEAULT, Bull. [3] 31, 1163 (1904). The autocondensation of two moles of the imino-ketone in the presence of zinc and acetic acid [according to the method described in Chimia 11, 310 (1957)] yielded 2,5-dimethyl-3,6-dibutyl-pyrazine which had a b.p. of 18° C./0.002 mm. Hg.

(5)

f. 2,5-Dimethyl-3,6-diisobutyl-pyrazine was prepared by first forming 5-methyl-3-oximino-2-hexanone by reacting 5-methyl-2-hexanone with nitrosyl chloride according to the method of BOUVEAULT (loc.cit.). The autocondensation of two moles of the imino-ketone in the presence of zinc and acetic acid [according to the method described in Chimia 11, 310 (1957)] yielded 2,5-dimethyl-3,6-diisobutyl-pyrazine which had a b.p. of 69°–70° C./0.01 mm. Hg.

(5)

g. 2,5-Dimethyl-3,6-diamyl-pyrazine was prepared by first forming 3-oximino-2-octanone by reacting 2-octanone with nitrosyl chloride according to the method of BOUVEAULT (loc.cit.). The autocondensation of two moles of the imino-ketone in the presence of zinc and acetic acid [according to the method described in Chimia 11, 310 (1957)] yielded 2,5-dimethyl-3,6-diamyl-pyrazine which had a b.p. of 78° C./0.03 mm. Hg.

(5)

h. 2,5-Dimethyl-3,6-dihexyl-pyrazine was prepared by first forming 3-oximino-2-nonanone by reacting 2-nonanone with nitrosyl chloride according to the method of BOUVEAULT (loc.cit.). The autocondensation of two moles of the imino-ketone in the presence of zinc and acetic acid [according to the method described in Chimia 11, 310 (1957)] yielded 2,5-dimethyl-3,6-dihexyl-pyrazine which had a b.p. of 112°–120° C./0.01 mm. Hg.

(5)

i. 2,3,5-Trimethyl-6-hexyl-pyrazine was prepared by introducing a hexyl group into the 6-position of 2,3,5-trimethylpyrazine by the method of Klein et al. (loc.cit.). The product had a b.p. of 89°–91° C./0.2 mm. Hg.

(5)

j. 2,5-Dimethyl-3,6-diethyl-pyrazine is prepared by alkylation of 2,5-dimethyl-3-ethyl-pyrazine according to the alkyl-lithium method described by Klein et al. [J.A.C.S. 73, 2949 (1951)]. It has a b.p. of 83°–85° C./8 mm. Hg.

(6)

a. 2-Ethyl-5-methyl-pyrazine was prepared by alkylation of 2,5-dimethyl-pyrazine following the procedure of Levine and Behun described in J.Org.Chem. 26, 3379 (1961). It has a boiling point of 60° C./11 mm. Hg.

(6)

b. 2-Isopropyl-5-methyl-pyrazine was produced in the preparation of compound (6) a. as a by-product and was separated from the reaction mixture by gas chromatography. Identification was confirmed by mass spectrometry.

(6)

c. 2,5-Diethyl-pyrazine was obtained by subjecting compound (6) a. to a second alkylation by the procedure given for compound (6) a. above. It boils at 64° C. at 12 mm. Hg.

(6)

d. 2-Methyl-5-vinyl-pyrazine was prepared by the method of Levine et al. described at J.Org.Chem. 27, 1363 (1962), starting from 2,5-dimethyl-pyrazine. It has a boiling point of 65°–66° C./12 mm. Hg.

ORGANOLEPTIC EVALUATIONS

As was described above, the compounds of this invention were subjected to organoleptic evaluation tests either in a syrup base (A), or one of the two soluble coffee bases (B and C). The following tables give the results of these organoleptic evaluations. In the tables, the column headed "Number" refers to the number of the test compound of the group. The column headed "Test" gives the Method of the Test, as described hereinbefore, and the column headed "Quantity" sets out the amount of the Test Compound used in grams per 100 liters of the base material.

ORGANOLEPTIC EVALUATION TABLES

TABLE I

| Number | Test | Quantity | Organoleptic Characterization |
|---|---|---|---|
| (1)a. | A | 0.3 | burnt, hardnut taste |
| (1)a. | B | 0.4 | enhanced the woody and coffee grounds note |
| (1)b. | A | 0.5 | green, vegetable-like |
| (1)b. | C | 0.17 | earthy, potato-like |
| (1)c. | A | 0.5 | earthy flavor |
| (1)c. | C | 0.2 | green; nitrobenzene |
| (1)d. | A | 0.5 | earthy, potato-like |
| (1)d. | B | 0.1–0.2 | enhanced the woody and coffee grounds notes; adds a bitter note |
| (1)d. | C | 0.084 | earthy; green; sulfury; mouthfeel |
| (1)e. | A | 0.25 | anise-like, liquorice flavor |
| (1)f. | A | 1.0 | hazelnut, coffee-like |
| (1)g. | A | 0.5 | anise-like |
| (1)h. | A | 2.0 | slight caramel flavor |
| (1)i. | A | 0.1 | earthy; potato; hazelnut taste |
| (1)i. | B | 0.01–0.02 | enhanced the coffee grounds note |
| (1)i. | C | 0.013 | earthy; green; acid |
| (1)j. | B | 0.06 | earthy; hazelnut; burnt taste |
| (1)k. | B | 0.45 | sweet; green; burnt; astringent note |
| (1)l. | A | 2.0 | earthy note |
| (1)m. | A | 4.0 | burnt; praline-like |
| (1)n. | A | 1.0 | green; burnt note |
| (1)o. | A | 4.0 | slight coffee taste; caramel; fruity |
| (1)p. | A | 4.0 | green, burnt note |
| (1)q. | A | 2.0 | burnt; coffee-like note |
| (1)r. | A | 0.3 | fresh; hazelnut; earthy note |
| (1)r. | C | 0.07 | earthy; green note |
| (2)a. | A | 3.0 | coffee-like taste |
| (2)b. | A | 0.5 | burnt almond taste |
| (2)b. | B | 0.2–0.4 | enhanced woody note |
| (2)c. | A | 2.0 | hazelnut taste |
| (2)d. | A | 4.0 | mild hazelnut taste |
| (2)e. | A | 1.0 | coffee-like taste |
| (2)e. | B | 1.0 | enhanced green and nutty notes |
| (2)f. | A | 3.0 | hazelnut, slightly burnt taste |
| (2)g. | A | 2.5 | caramel-like, fruity taste |
| (2)h. | A | 0.5 | green floral taste |
| (2)i. | A | 1.0 | anise-like taste |
| (2)j. | A | 0.5 | hazelnut-like taste |
| (3)a. | A | 1.0 | burnt, roasted hazelnut-like taste |
| (3)a. | C | 0.27 | toasted |
| (3)b. | A | 4.0 | phenolic, burnt taste |
| (3)c. | A | 4.0 | burnt, earthy taste |
| (3)d. | B | 2.5 | astringent; fatty; earthy |
| (3)e. | B | 0.7 | hazelnut-like; bitter; roasted |
| (3)f. | B | 0.6 | bitter; earthy |

TABLE I-continued

| Number | Test | Quantity | Organoleptic Characterization |
|---|---|---|---|
| (3)g. | B | 2.5 | bitter; acid; earthy |
| (3)h. | B | 1.2 | bitter; astringent |
| (3)i. | B | 2.5 | bitter; acid; woody |
| (3)j. | B | 1.2 | bitter; earthy; woody |
| (3)k. | B | 1.2 | bitter; earthy; fatty |
| (3)l. | B | 2.0 | green; roasted |
| (4)a. | A | 2.0 | roasted hazelnut-like taste |
| (4)b. | A | 1.0 | burnt, hazelnut-like taste |
| (4)b. | B | 1.0 | enhanced the green nutty note |
| (4)c. | A | 0.5 | hazelnut-like taste |
| (4)d. | A | 4.0 | fresh hazelnut taste |
| (5)a. | A | 1.5 | caramel- and coffee-like |
| (5)b. | A | 1.5 | anise-like, floral taste |
| (5)c. | A | 3.0 | hazelnut; slightly acid |
| (5)d. | A | 3.0 | burnt, phenolic taste |
| (5)e. | A | 4.0 | fatty taste |
| (5)f. | A | 3.0 | maple-like taste |
| (5)g. | A | 1.0 | fatty taste, slightly reminiscent of chocolate |
| (5)h. | A | 1.0 | green fatty, burnt taste |
| (5)i. | A | 5.0 | fatty, hazelnut-like taste |
| (5)j. | A | 1.0 | coffee-like; green; earthy |
| (6)a. | A | 2.0 | coffee-like taste |
| (6)b. | A | 0.5 | green taste |
| (6)c. | A | 1.0 | hazelnut-like taste |
| (6)d. | A | 1.0 | coffee-like taste |

As has been stated above the compounds having utility in the concept of this invention may be added to substances in varying amounts to alter or to modify the flavor of the substance by masking or blanking out undesirable flavors, by enhancing or fortifying desirable flavor or flavor notes, or by adding to the original substance an entirely new and different flavor. As will also be apparent to those skilled in the art various mixtures or blends of the flavor agents described may be used to achieve a desired flavor or flavor note. If, for example, one wishes to enhance a certain flavor note, or group or flavor notes present in a substance such as coffee, one needs only mix together certain of the described flavor agents to obtain the desired result.

Following are three examples of mixtures that have been prepared in accordance with the inventive concept.

TABLE II

| Compound Name | Parts by weight | | |
|---|---|---|---|
| | Ex. 1 | Ex. 2 | Ex. 3 |
| 2-methyl-3-ethyl-pyrazine | — | 40 | 20 |
| 2,3-diethyl-pyrazine | — | — | 0.5 |
| 2-methyl-3-isopropyl-pyrazine | 5 | 5 | 7.5 |
| 2-acetyl-pyrazine | — | 30 | 10 |
| 2-methyl-3-methylthio-pyrazine | 2 | — | 2 |
| furfurylthiol acetate | 2 | 2 | 3 |
| furfuryl methyl sulfide | — | 1 | — |
| 2-acetyl thiophene | — | 80 | — |
| furfuryl propyl sulfide | — | 3 | 1 |
| 2,6-dimethyl-γ-thiopyrene | 4 | 4 | 4 |
| 2-methoxybenzenethiol | — | 12 | 6 |
| 2-hydroxyphenyl methyl sulfide | 1 | 2 | 1.5 |
| 3,4-xylenol | 4 | 4 | 2 |
| 2-hydroxyacetophenone | — | — | 5 |
| 4-ethyl-2-methoxy-phenol | — | 5 | 2.5 |
| 4-ethyl-phenol | — | — | 0.5 |
| pyridine | 20 | 30 | 20 |
| 2-vinyl-benzofuran | 3 | 3 | 4 |
| 4-vinyl-1,2-dimethoxy benzene | — | 40 | — |
| furfuryl propionate | — | 50 | — |
| furfural | — | 100 | — |

When added to a commercially available soluble powdered coffee beverage these blends of flavor agents added flavor notes which enhanced the flavor of the soluble coffee in the direction of that of roasted and ground coffee which has been brewed into a coffee beverage.

In order to demonstrate the flavor modifying or enhancing effect of the compounds of this invention a base material having the following composition was prepared:

| Compound | Parts by weight |
|---|---|
| 3-methyl-cyclopentane-1,2-dione | 50 |
| furfuryl alcohol | 50 |
| furfural | 10 |
| diacetyl | 5 |
| acetylmethylcarbinol | 30 |
| benzyl alcohol | 100 |
| propylene glycol | 755 |
| | 1000 |

Compounds of this invention were added to this base in varying amounts and the resulting compound mixtures were used to enhance or modify the flavor of the following food products:

(a) A solution of milk sweetened with sugar, at a dosage level of 10 grams of the flavor composition per 100 kg.
(b) A prepared ice-cream, at a dosage level of 10–15 g. of flavor composition per 100 kg.
(c) A white cake mix, at a level of 20 g. per 100 kg. of finished cake
(d) A milk pudding, at a dosage level of 10–15 g. per 100 kg.
(e) A milk chocolate, at a dosage level of 25 g. per 100 kg.

A number of the compounds of the group were added to the above described base material. The resulting compound mixtures had the formulations shown in Table III below.

When added to the food products at the dosage levels as described in above, the compound mixtures of Examples 4–11 imparted a pronounced nutty, green, fresh, earthy flavor note, with a light note of coffee groups, to the foods.

Further compound mixtures utilizing mixtures of pyrazine sulfur compounds and pyrazine hydrocarbon compounds were made as set out in Table IV below.

TABLE IV

| Compound Name | Parts by Weight Examples | | | |
|---|---|---|---|---|
| | 12 | 13 | 14 | 15 |
| (2) 2-pyrazinyl-ethyl-mercaptan | 20 | 20 | 20 | 20 |
| (2) 2-pyrazinyl-ethyl furfuryl sulfide | 20 | 20 | 20 | 20 |
| (1) 2-methyl-3-ethyl-pyrazine | — | — | 10 | 10 |
| (1) 2-methyl-3-propyl pyrazine | — | — | 20 | 5 |
| (1) 2,3-diethyl-pyrazine (10% solution) | — | 10 | — | 5 |
| 3-methyl-cyclopentane-1,2-dione | 50 | 50 | 50 | 50 |
| furfuryl alcohol | 50 | 50 | 50 | 50 |
| furfural | 10 | 10 | 10 | 10 |
| diacetyl | 5 | 5 | 5 | 5 |
| acetylmethylcarbinol | 30 | 30 | 30 | 30 |
| benzyl alcohol | 100 | 100 | 100 | 100 |
| propylene glycol | 715 | 705 | 685 | 695 |
| | 1000 | 1000 | 1000 | 1000 |

When added to the same food products as above and in the same dosage levels, the foods were found to have their flavor modified to one with a definite coffee flavor with a light touch of a coffee grounds note.

Some further compound mixtures were prepared from pyrazine hydrocarbon compounds using as a base the following mixture:

| | Parts by weight |
|---|---|
| 3-methyl-cyclopentane-1,2-dione | 200 |
| Essence of cinnamon | 10 |
| Essence of sweet fennel | 20 |
| Essence of star anise | 20 |
| benzyl alcohol | 250 |
| propylene glycol | 500 |
| | 1000 |

TABLE III

| Compound Name | Parts by weight Examples | | | | | | | |
|---|---|---|---|---|---|---|---|---|
| | 4 | 5 | 6 | 7 | 8 | 9 | 10 | 11 |
| 2,3-dimethyl-pyrazine | 250 | — | — | — | — | — | 50 | — |
| 2-methyl-3-ethyl-pyrazine | — | 25 | — | — | — | 20 | 15 | 10 |
| 2-methyl-3-propyl-pyrazine | — | — | 45 | — | — | 25 | — | 15 |
| 2-methyl-3-isopropyl-pyrazine | — | — | — | 45 | — | — | — | 20 |
| 2-ethyl-3-ethyl-pyrazine (10% soln.) | — | — | — | — | 10 | — | 5 | 2 |
| 3-methyl-cyclopentane-1,2-dione | 50 | 50 | 50 | 50 | 50 | 50 | 50 | 50 |
| furfuryl alcohol | 50 | 50 | 50 | 50 | 50 | 50 | 50 | 50 |
| furfural | 10 | 10 | 10 | 10 | 10 | 10 | 10 | 10 |
| diacetyl | 5 | 5 | 5 | 5 | 5 | 5 | 5 | 5 |
| acetylmethylcarbinol | 30 | 30 | 30 | 30 | 30 | 30 | 30 | 30 |
| benzyl alcohol | 100 | 100 | 100 | 100 | 100 | 100 | 100 | 100 |
| propylene glycol | 505 | 730 | 710 | 710 | 745 | 710 | 685 | 708 |
| | 1000 | 1000 | 1000 | 1000 | 1000 | 1000 | 1000 | 1000 |

The exact formulations of these compound mixtures are set out in Table V below.

TABLE V

| Compound Name | Parts by weight Examples | | | | |
|---|---|---|---|---|---|
| | 16 | 17 | 18 | 19 | 20 |
| (1) 2-methyl-3-butyl-pyrazine | 25 | — | — | — | 5 |
| (1) 2-methyl-3-isobutyl-pyrazine | — | 50 | — | — | 15 |
| (1) 2-methyl-3-amyl-pyrazine | — | — | 100 | — | 20 |
| (1) 2-methyl-3-hexyl-pyrazine | — | — | — | 50 | 15 |
| 3-methyl-cyclopentane-1,2-dione | 200 | 200 | 200 | 200 | 200 |
| Essence of cinnamon | 10 | 10 | 10 | 10 | 10 |
| Essence of sweet fennel | 20 | 20 | 20 | 20 | 20 |
| Essence of star anise | 20 | 20 | 20 | 20 | 20 |
| benzyl alcohol | 250 | 250 | 250 | 250 | 250 |
| propylene glycol | 475 | 450 | 400 | 450 | 445 |
| | 1000 | 1000 | 1000 | 1000 | 1000 |

When added to a soft gum-drop candy formulation at a dosage level of 30 g. per 100 kg., to an ice-cream mix at a dosage level of 8–10 g. per 100 kg., to a milk pudding mix at a dosage level of 8–10 g. per 100 kg., and to a hard candy formulation at a dosage level of 15–20 g. per 100 kg., the compound mixtures imparted a definite anise, liquorice-like flavor note to the finished products.

It should be kept in mind, as will be appreciated by those skilled-in-the-art, that with many flavors it is possible to imitate the natural flavor by selecting a limited number of the flavor enhancing substances examplified above. Coffee aroma, on the other hand, is much more complex than the ordinary flavoring materials and may necessitate the combination of many more of the examplified ingredients for reproduction.

It will also be understood that whereas the preferred embodiment of this invention is directed toward the enhancement or modification of coffee flavors, the concept of the invention has much wider application. While some of the compounds may be characterized by terms which are not directly related to coffee flavors, these compounds, when used in more complex formulae, may contribute desirable flavor notes to the overall flavor and aroma.

To summarize briefly this invention relates to a group of chemical compounds which have been found to have utility for the alteration or modification of the flavor or other materials. These compounds, called flavor agents or flavor modifiers, may be used in minute quantities to enhance the natural flavor of substances to which they are added, or to alter or modify a flavor which is undesirable, or to impart to a substance additional or different flavors or flavor notes. The flavor agents of the invention are used in minor, but flavor altering amounts, in any case, in quantities sufficient to obtain the desired results. The flavor modifiers are of particular importance and usefulness in the modification, alteration or enhancement of the flavor of coffee beverages made from soluble coffee and the preferred embodiment of the invention contemplates their use in conjunction with such products.

The flavor agents of the invention may be added at a convenient step in the soluble coffee process such as plating the dried soluble coffee with a desired dilution of the flavor agent in an acceptable solution followed by drying. In certain instances the desired agent may be added directly to a concentrate coffee extract and the mixture dried into a soluble coffee product which contains the flavor agent as an integral part thereof. Other methods of incorporation of the agents will suggest themselves to those skilled in the art and may, of course, be used without departing from the inventive concept, which may be described as being a composition of matter comprising a combination of a soluble coffee product, however prepared, whether liquid or solid, concentrated or dilute, which contains combined therewith a minor, but flavor modifying amount, of a flavor agent as described herein.

What is claimed is:

1. A foodstuff having added thereto a small but flavor-modifying amount of a compound consisting essentially of a pyrazine derivative having the following formula:

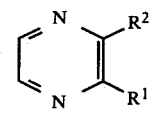

wherein
(a) $R^1$ is a methyl group and $R^2$ is either an alkyl group having from 2 to 6 carbon atoms which can be branched at the chain end when said chain has 3 or 4 carbon atoms, or a vinyl, a thienyl-2 or a pyrryl-1 group; or
(b) $R^1$ is an ethyl group and $R^2$ is an ethyl or a vinyl group.

2. Soluble coffee having added thereto a small but flavor-modifying amount of a compound consisting essentially of a pyrazine derivative having the following formula:

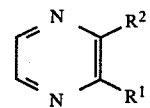

wherein
(a) $R^1$ is a methyl group and $R^2$ is either an alkyl group having from 2 to 6 carbon atoms which can be branched at the chain end when said chain has 3 or 4 carbon atoms, or a vinyl, a thienyl-2 or a pyrryl-1 group; or
(b) $R^1$ is an ethyl group and $R^2$ is an ethyl or a vinyl group.

3. The process of imparting a roasted, nutty, popcorn-like flavor or aroma to a foodstuff which comprises adding thereto a small but effective amount of 2-methyl-3-ethyl pyrazine.

* * * * *